United States Patent [19]

Stoltefuss et al.

[11] Patent Number: 5,051,433
[45] Date of Patent: * Sep. 24, 1991

[54] PHARMACEUTICALLY ACTIVE BASIC NITRO-PHENYL-DIHYDROPYRIDINE AMIDES

[75] Inventors: Jürgen Stoltefuss, Haan; Eckhard Schwenner, Wuppertal; Rainer Gross, Wuppertal; Siegbert Hebisch, Wuppertal; Matthias Schramm, Cologne; Martin Bechem, Wuppertal; Claudia Hirth, Wuppertal; Johannes-Peter Stasch, Wuppertal, all of Fed. Rep. of Germany

[73] Assignee: Bayer Aktiengesellschaft, Leverkusen, Fed. Rep. of Germany

[*] Notice: The portion of the term of this patent subsequent to May 14, 2008 has been disclaimed.

[21] Appl. No.: 413,510

[22] Filed: Sep. 27, 1989

[30] Foreign Application Priority Data

Oct. 5, 1988 [DE] Fed. Rep. of Germany ....... 3833893

[51] Int. Cl.$^5$ ............................................. A61K 31/455
[52] U.S. Cl. .................................... 514/356; 546/321
[58] Field of Search ........................ 546/321; 514/356

[56] References Cited

U.S. PATENT DOCUMENTS

| 4,256,749 | 3/1981 | Horstmann et al. | 546/321 |
| 4,492,703 | 1/1985 | Goldmann et al. | 546/321 |
| 4,769,465 | 9/1988 | Antoncic et al. | 546/321 |
| 4,874,773 | 10/1989 | Hisaki et al. | 514/355 |

FOREIGN PATENT DOCUMENTS 0179386 4/1986 European Pat. Off. .
0280239 8/1988 European Pat. Off. .

OTHER PUBLICATIONS

Takenaka et al., CA 108: 160946q.
Kazuo et al., CA 85: 78008h.

*Primary Examiner*—Jane T. Fan
*Attorney, Agent, or Firm*—Sprung Horn Kramer & Woods

[57] ABSTRACT

Hypertension and cardiac insufficiency can be controlled by 4-nitrophenyl-dihydropyridine amides of the formula

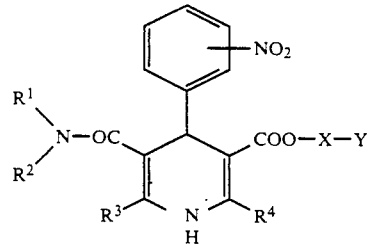

in which
X can be ethylene or the like,
Y is pyridyl or $-NR^9R^{10}$, and
$R^9$ and $R^{10}$ each independently is hydrogen or an organic group, or together form a ring, and physiologically tolerated salts thereof. Compounds in which $R^5$ and $R^6$ are not aryl or aralkyl are new.

4 Claims, No Drawings

PHARMACEUTICALLY ACTIVE BASIC NITRO-PHENYL-DIHYDROPYRIDINE AMIDES

The present invention relates to the use of nitro-phenyl-dihydropyridine amides, some of which are known, as medicaments, new active compounds and processes for their preparation via new intermediates, in particular use as circulation-influencing medicaments.

It has already been disclosed that basic 4-aryldihydropyridine amines are employed as intermediates for the preparation of 1,4-dihydropyridine-hydroxyalkylamines [cf. EP-A 0,179,386].

In this publication, dihydropyridine derivatives are described which carry a hydroxyalkylamine ester group in the 3-position. The substituent X in the 5-position also includes amide radicals in its general meaning. The active compounds described therein are prepared, inter alia, via dihydropyridine amines of the general formula (II) which are employed therein as intermediates. The general definition of these intermediates of the formula (II) also includes, inter alia, dihydropyridine amides without, however, naming an actual representative of this class of substance. This publication also contains no indication of any pharmacological action of those intermediates employed therein.

In DE-OS (German Offenlegungsschrift) 2,228,377, dihydropyridinecarboxylic acid amides, a number of processes for their preparation and their use as circulation-influencing agents are described. The compounds mentioned therein differ from the active compounds according to the invention in that the 3- and 5-positions of the dihydropyridine ring either both simultaneously carry an amide group or one of these positions carries an ester group which, however, in turn no longer contains basic groups. In contrast thereto, the ester radical of the compounds to be used according to the invention always contains a basic radical (see definition of X and Y).

Dihydropyridine derivatives are also described in EP-A 0,220,653 which contain an amide group in the 3-position and an ester group in the 5-position. In these cases also, the ester group no longer carries a basic radical. These known monoamides also possess circulatory effects.

It has been found that the 4-nitrophenyl-dihydropyridine amides of the general formula (I)

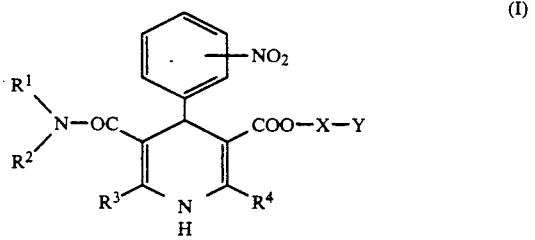

in which $R^1$ and $R^2$ are identical or different and
  denote hydrogen, or
  represent cycloalkyl having 3 to 8 carbon atoms, or
  represent straight-chain or branched alkyl or alkenyl, in each case having up to 12 carbon atoms, which are optionally substituted by halogen, hydroxyl, alkoxy having up to 8 carbon atoms, alkylthio having up to 8 carbon atoms, alkylcarbonyl having up to 8 carbon atoms, carboxyl or alkoxycarbonyl having up to 8 carbon atoms or by phenyl which may in turn be substituted by halogen, nitro, cyano, trifluoromethyl, trifluoromethoxy, alkyl having up to 4 carbon atoms or alkoxy having up to 4 carbon atoms or by an $-NR^5R^6$ group, in which $R^5$ and $R^6$ are identical or different and denote hydrogen, alkyl having up to 8 carbon atoms, aryl or aralkyl,
  represent phenyl which may be monosubstituted to trisubstituted by identical or different substituents from the series comprising nitro, cyano, halogen, alkyl having up to 6 carbon atoms, alkoxy having up to 6 carbon atoms, alkylthio having up to 6 carbon atoms, trifluoromethyl, trifluoromethoxy, difluoromethoxy, trifluoromethylthio, amino, alkylamino having up to 8 carbon atoms per alkyl group, dialkylamino having up to 8 carbon atoms per alkyl group, acetylamino or benzoylamino, or $R^1$ and $R^2$ together form a 5- to 7-membered saturated or unsaturated heterocyclic ring which may contain an oxygen atom, a sulphur atom or a nitrogen atom as an additional heteroatom, or an $N-R^7$ radical, in which $R^7$—may denote hydrogen, $C_1-C_6$-alkyl, aryl or aralkyl and $R^3$ and $R^4$ are identical or different and
  represent straight-chain, branched or cyclic alkyl having up to 8 carbon atoms which is optionally substituted by hydroxyl, cyano, phenyl or halogen, and X—represents a straight-chain, branched or cyclic, saturated or unsaturated hydrocarbon radical having up to 12 carbon atoms which is optionally interrupted by an oxygen, sulphur or nitrogen atom, or by an $N-R^8$ group, in which $R^8$—denotes hydrogen, or
  represents alkyl having up to 6 carbon atoms which is optionally substituted by halogen, hydroxyl, acetoxy, carboxyl, $C_1-C_8$-alkoxy carbonyl or phenyl which may in turn be substituted by halogen, $C_1-C_6$-alkyl, $C_1-C_6$-alkoxy, halomethyl, halomethoxy or cyano, and Y—denotes pyridyl, or
  represents a group of the formula $-NR^9R^{10}$, in which $R^9$ and $R^{10}$ are identical or different and
  denote hydrogen, or
  represent straight-chain or branched alkyl, alkenyl or alkinyl in each case having up to 12 carbon atoms, which may be substituted by halogen, hydroxyl, alkoxy having up to 8 carbon atoms, cyano, trifluoromethyl, alkylthio having up to 8 carbon atoms, alkylcarbonyl having up to 8 carbon atoms, alkoxycarbonyl having up to 8 carbon atoms or by phenyl which may in turn be substituted by nitro, phenyl, cyano, trifluoromethyl, trifluoromethoxy, alkyl having up to 4 carbon atoms, halogen or alkoxy having up to 4 carbon atoms, or
  represent cycloalkyl having 3 to 8 carbon atoms, or
  represent aryl having 6 to 10 carbon atoms which may be monosubstituted to trisubstituted by identical or different substituents from the series comprising nitro, cyano, halogen, alkyl having up to 6 carbon atoms, alkoxy having up to 6 carbon atoms, alkylthio having up to 6 carbon atoms, carbamoyl, dialkylcarbamoyl in each case having up to 6 carbon atoms per alkyl group, trifluoromethyl, trifluoromethoxy, difluoromethoxy, trifluoromethylthio, amino, alkylamino having up to 8 carbon atoms or dialkylamino in each case having up to 8 carbon atoms per alkyl group, or $R^9$ and $R^{10}$ together form a 5- to 7-membered, saturated or unsaturated heterocyclic ring which may contain an oxygen atom, a sulphur atom or an additional nitrogen atom which is optionally substituted by an $R^{11}$ radical, in which $R^{11}$—represents hydrogen, or represents a straight-chain or branched, saturated or unsaturated alkenylene group having up to 10 carbon atoms which is optionally substituted by phenyl which may in turn be substituted by halogen, $C_1$-$C_4$-alkyl, $C_1$-$C_4$-alkoxy, nitro or haloalkyl having up to 4 carbon atoms or, represents phenyl which is optionally substituted by halogen, cyano, nitro, alkyl having up to 4 carbon atoms, alkoxy having up to 4 carbon atoms or haloalkyl having up to 4 carbon atoms, surprisingly also show a strong antiarrhythmic action in addition to the expected calcium antagonist activity and influence the salt and liquid balance and are thus suitable for use in the control of hypertonia and cardiac insufficiency.

The physiologically acceptable acid addition salts of the compounds of the general formula (I) and the racemic forms, the antipodes and the diastereomer mixtures are also preferably suitable for this new use.

Compounds of the general formula (I) are preferably used in which $R^1$ and $R^2$ are identical or different and denote hydrogen or represent cycloalkyl having 3 to 8 carbon atoms, or represent straight-chain or branched alkyl or alkenyl, in each case having up to 10 carbon atoms, which are optionally substituted by fluorine, chlorine, hydroxyl, $C_1$-$C_6$-alkoxy, $C_1$-$C_6$-alkylthio, $C_1$-$C_6$-alkylcarbonyl, $C_1$-$C_6$-alkoxycarbonyl, carboxyl or by phenyl which may in turn be substituted by halogen, nitro, cyano, trifluoromethyl, trifluoromethoxy, methyl or methoxy or by a group of the formula —$NR^5R^6$, in which $R^5$ and $R^6$ are identical or different and represent hydrogen, $C_1$-$C_6$-alkyl, benzyl, phenethyl or phenyl, represent phenyl which is optionally monosubstituted or disubstituted by identical or different substituents from the series comprising fluorine, chlorine, $C_1$-$C_4$-alkyl, $C_1$-$C_4$-alkoxy, $C_1$-$C_4$-alkylthio, trifluoromethyl, trifluoromethoxy or difluoromethoxy, or $R^1$ and $R^2$ together represent pyridyl, pyrrolidyl, piperidyl or morpholinyl, or represent piperazinyl which is optionally substituted by $C_1$-$C_4$-alkyl, benzyl or phenethyl, $R^3$ and $R^4$ are identical or different and represent straight-chain or branched alkyl having up to 6 carbon atoms which is optionally substituted by fluorine, chlorine, phenyl or hydroxyl, X—represents a straight-chain, branched or cyclic, saturated or unsaturated hydrocarbon radical having up to 10 carbon atoms which is optionally interrupted by an oxygen, a sulphur or a nitrogen atom, or by an N—$R^8$ radical, in which $R^8$—denotes hydrogen, or represents $C_1$-$C_4$-alkyl which is optionally substituted by fluorine, chlorine, hydroxyl, carboxyl or by phenyl which may in turn be substituted by fluorine, chlorine, $C_1$-$C_4$-alkyl, $C_1$-$C_4$-alkoxy, trifluoromethyl or trifluoromethoxy, and Y—denotes pyridyl, or represents a group of the formula —$NR^9R^{10}$, in which $R^9$ and $R^{10}$ are identical or different and denote hydrogen, or represent straight-chain or branched alkyl or alkenyl in each case having up to 8 carbon atoms which may be substituted by fluorine, chlorine, hydroxyl, $C_1$-$C_4$-alkoxy, $C_1$-$C_4$-alkylthio, $C_1$-$C_4$-alkylcarbonyl, carboxyl or $C_1$-$C_6$-alkoxycarbonyl, or by phenyl which may in turn be substituted by trifluoromethyl, $C_1$-$C_2$-alkyl, fluorine, chlorine or $C_1$-$C_2$-alkoxy, or represent cycloalkyl having 3 to 8 carbon atoms, or represent phenyl which may be monosubstituted or disubstituted by identical or different substituents from the series comprising nitro, cyano, fluorine, chlorine, bromine, $C_1$-$C_4$-alkyl, $C_1$-$C_4$-alkoxy, $C_1$-$C_4$-alkylthio, trifluoromethyl, trifluoromethoxy, difluoromethoxy, trifluoromethylthio, amino or alkylamino having up to 4 carbon atoms, or $R^9$ and $R^{10}$ together form a 5- to 7-membered saturated or unsaturated heterocyclic ring which may additionally contain an oxygen or sulphur atom or an additional nitrogen atom which is optionally substituted by an $R^{11}$ radical, in which $R^{11}$—represents hydrogen or represents a straight-chain or branched, saturated or unsaturated alkyl group having up to 4 carbon atoms, which is optionally substituted by phenyl which may in turn be substituted by fluorine, chlorine, $C_1$-$C_2$-alkyl, $C_1$-$C_2$-alkoxy or $C_1$-$C_2$-haloalkyl, or represents phenyl which is optionally substituted by fluorine, chlorine, cyano, $C_1$-$C_2$-alkyl, $C_1$-$C_2$-alkoxy or $C_1$-$C_2$-haloalkyl, and their physiologically acceptable salts for the control of hypertonia and cardiac insufficiency.

Compounds of the general formula (I) are particularly preferably used in which $R^1$ and $R^2$ are identical or different and represent hydrogen, cyclopropyl, cyclopentyl or cyclohexyl, or represent straight-chain or branched alkyl or alkenyl having up to 8 carbon atoms, which is optionally substituted by fluorine, chlorine, hydroxyl, $C_1$-$C_4$-alkoxy, $C_1$-$C_4$-alkylthio, carboxyl, $C_1$-$C_4$-alkoxycarbonyl or by phenyl which may in turn be substituted by chlorine, fluorine, methyl or methoxy, or represent phenyl which may be substituted by fluorine, chlorine, methyl, ethyl, methoxy, trifluoromethyl or trifluoromethoxy, $R^3$ $R^4$—represent methyl and X—represents a straight-chain, branched or cyclic, saturated or unsaturated hydrocarbon radical having up to 8 carbon atoms, which is optionally interrupted by an oxygen, sulphur or nitrogen atom, or by an —N—$R^8$ radical, in which $R^8$—denotes hydrogen, or represents methyl, ethyl, benzyl, phenethyl or phenyl which is optionally substituted by fluorine, chlorine, methyl, methoxy, trifluoromethyl or trifluoromethoxy, Y—represents pyridyl, or represents a group of the formula —NR$^9$R$^{10}$ in which R$^9$ and R$^{10}$ are identical or different and denote hydrogen, or represent straight-chain or branched alkyl or alkenyl having up to 4 carbon atoms which may be substituted by fluorine, chlorine, hydroxyl, C$_1$-C$_4$-alkoxycarbonyl or by phenyl which may in turn be substituted by fluorine, chlorine, trifluoromethyl, methyl or methoxy, or represent cyclopropyl, cyclopentyl or cyclohexyl, or represent phenyl which may be monosubstituted or disubstituted by identical or different substituents from the series comprising fluorine, chlorine, methyl, ethyl, methoxy, ethoxy, methylthio, trifluoromethyl, trifluoromethoxy, difluoromethoxy, amino, C$_1$-C$_2$-alkylamino or C$_1$-C$_2$-dialkylamino, or R$^9$ and R$^{10}$ together form a 5- to 7-membered saturated ring which may additionally contain an oxygen, sulphur or an additional nitrogen atom which is optionally substituted by an R$^{11}$ radical in which R$^{11}$—represents hydrogen, C$_1$-C$_4$-alkyl, benzyl or phenethyl, or represents phenyl which may be substituted by fluorine, chlorine, methyl or methoxy, and their physiologically acceptable salts in the control of hypertonia and cardiac insufficiency.

The compounds according to the invention show an unforeseeable useful spectrum of pharmacological action. They influence the contractility of the heart, the tone of the smooth musculature and the electrolyte and fluid balance.

They can therefore be used for the preparation of medicaments for the treatment of pathologically changed blood pressure and cardiac insufficiency, and also of coronary therapeutics.

Moreover, they can be employed in the preparation of medicaments for the treatment of cardiac arrhythmias, renal insufficiency, cirrhosis of the liver, ascites, pulmonary oedema, cerebral oedema, oedema of pregnancy, glaucoma or diabetes mellitus.

The invention in addition relates to 4-nitrophenyl-dihydropyridine amides of the general formula (Ia)

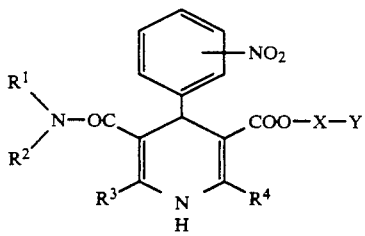

(Ia)

in which

R$^1$ and R$^2$ are identical or different and denote hydrogen, or represent cycloalkyl having 3 to 8 carbon atoms, or represent straight-chain or branched alkyl or alkenyl, in each case having up to 12 carbon atoms, which are optionally substituted by halogen, hydroxyl, alkoxy having up to 8 carbon atoms, alkylthio having up to 8 carbon atoms, alkylcarbonyl having up to 8 carbon atoms, carboxyl or alkoxycarbonyl having up to 8 carbon atoms or by phenyl which may in turn be substituted by halogen, nitro, cyano, trifluoromethyl, trifluoromethoxy, alkyl having up to 4 carbon atoms or alkoxy having up to 4 carbon atoms or by an —NR$^5$R$^6$ group, in which R$^5$ and R$^6$ are identical or different and denote hydrogen or alkyl having up to 8 carbon atoms, represent phenyl which may be monosubstituted to trisubstituted by identical or different substituents from the series comprising nitro, cyano, halogen, alkyl having up to 6 carbon atoms, alkoxy having up to 6 carbon atoms, alkylthio having up to 6 carbon atoms, trifluoromethyl, trifluoromethoxy, difluoromethoxy, trifluoromethylthio, amino, alkylamino having up to 8 carbon atoms, dialkylamino having up to 8 carbon atoms per alkyl group, acetylamino or benzoylamino, or R$^1$ and R$^2$ together form a 5- to 7-membered saturated or unsaturated heterocyclic ring which may contain an oxygen atom, a sulphur atom or a nitrogen atom as an additional heteroatom, or an N—R$^7$ radical, in which R$^7$—may denote hydrogen, C$_1$-C$_6$-alkyl, aryl or aralkyl and R$^3$ R$^4$ are identical or different and represent straight-chain, branched or cyclic alkyl having up to 8 carbon atoms which is optionally substituted by hydroxyl, cyano, phenyl or halogen, and X—represents a straight-chain, branched or cyclic, saturated or unsaturated hydrocarbon radical having up to 12 carbon atoms which is optionally interrupted by an oxygen, sulphur or nitrogen atom, or by an N—R$^8$ group, in which R$^8$—denotes hydrogen, or represents alkyl having up to 6 carbon atoms which is optionally substituted by halogen, hydroxyl, acetoxy, carboxyl, C$_1$-C$_8$-alkoxycarbonyl or phenyl which may in turn be substituted by halogen, C$_1$-C$_6$-alkyl, C$_1$-C$_6$-alkoxy, halomethyl, halomethoxy or cyano, and Y—denotes pyridyl, or represents a group of the formula —NR$^9$R$^{10}$, in which R$^9$ and R$^{10}$ are identical or different and represent hydrogen or straight-chain or branched alkyl, alkenyl or alkinyl in each case having up to 12 carbon atoms, which may be substituted by halogen, hydroxyl, alkoxy having up to 8 carbon atoms, cyano, trifluoromethyl, alkylthio having up to 8 carbon atoms, alkylcarbonyl having up to 8 carbon atoms, alkoxycarbonyl having up to 8 carbon atoms or by phenyl which may in turn be substituted by nitro, phenyl, cyano, trifluoromethyl, trifluoromethoxy, alkyl having up to 4 carbon atoms, halogen or alkoxy having up to 4 carbon atoms, or represent cycloalkyl having 3 to 8 carbon atoms, or represent aryl having 6 to 10 carbon atoms which may be monosubstituted to trisubstituted by identical or different substituents from the series comprising nitro, cyano, halogen, alkyl having up to 6 carbon atoms, alkoxy having up to 6 carbon atoms, alkylthio having up to 6 carbon atoms, carbamoyl, dialkylcarbamoyl in each case having up to 6 carbon atoms per alkyl group, trifluoromethyl, trifluoromethoxy, difluoromethoxy, trifluoromethylthio, amino, alkylamino having up to 8 carbon atoms or dialkylamino in each case having up to 8 carbon atoms per alkyl group, or $R^9$ and $R^{10}$ together form a 5- to 7-membered, saturated or unsaturated heterocyclic ring which may contain an oxygen atom, a sulphur atom or an additional nitrogen atom which is optionally substituted by an $R^{11}$ radical, in which $R^{11}$—represents hydrogen, or represents a straight-chain or branched, saturated or unsaturated alkenylene group having up to 10 carbon atoms which is optionally substituted by phenyl which may in turn be substituted by halogen, $C_1$-$C_4$-alkyl, $C_1$-$C_4$-alkoxy, nitro or haloalkyl having up to 4 carbon atoms, or represents phenyl which is optionally substituted by halogen, cyano, nitro, alkyl having up to 4 carbon atoms, alkoxy having up to 4 carbon atoms or haloalkyl having up to 4 carbon atoms, and their physiologically acceptable salts.

The compounds according to the invention exist in stereoisomeric forms which either behave as image and mirror image (enantiomers) or which do not behave as image and mirror image (diastereomers). The invention relates both to the antipodes and to the racemic forms and also to the diastereomer mixtures. The racemic forms, like the diastereomers, can be separated in a known manner into the stereoisomerically uniform components (cf. E. L. Eliel, Stereochemistry of Carbon Compounds, McGraw Hill, 1962).

Physiologically acceptable salts may be salts of the compounds according to the invention with inorganic or organic acids. Salts with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid are preferred.

Compounds of the general formula (Ia) are preferred in which $R^1$ and $R^2$ are identical or different and denote hydrogen or represent cycloalkyl having 3 to 8 carbon atoms, or represent straight-chain or branched alkyl or alkenyl, in each case having up to 10 carbon atoms, which are optionally substituted by fluorine, chlorine, hydroxyl, $C_1$-$C_6$-alkoxy, $C_1$-$C_6$-alkylthio, $C_1$-$C_6$-alkylcarbonyl, $C_1$-$C_6$-alkoxycarbonyl, carboxyl or by phenyl which may in turn be substituted by halogen, nitro, cyano, trifluoromethyl, trifluoromethoxy, methyl or methoxy or by a group of the formula —$NR^5R^6$, in which $R^5$ and $R^6$ are identical or different and represent hydrogen, $C_1$-$C_6$-alkyl, benzyl, phenethyl or phenyl, represent phenyl which is optionally monosubstituted or disubstituted by identical or different substituents from the series comprising fluorine, chlorine, $C_1$-$C_4$-alkyl, $C_1$-$C_4$-alkoxy, $C_1$-$C_4$-alkylthio, trifluoromethyl, trifluoromethoxy or difluoromethoxy, or $R^1$ and $R^2$ together represent pyridyl, pyrrolidyl, piperidyl or morpholinyl, or represent piperazinyl which is optionally substituted by $C_1$-$C_4$-alkyl, benzyl or phenethyl, $R^3$ and $R^4$ are identical or different and represent straight-chain or branched alkyl having up to 6 carbon atoms which is optionally substituted by fluorine, chlorine, phenyl or hydroxyl, X—represents a straight-chain, branched or cyclic, saturated or unsaturated hydrocarbon radical having up to 10 carbon atoms which is optionally interrupted by an oxygen, a sulphur or a nitrogen atom, or by an N—$R^8$ radical, in which $R^8$—denotes hydrogen, or represents $C_1$-$C_4$-alkyl which is optionally substituted by fluorine, chlorine, hydroxyl, carboxyl or by phenyl which may in turn be substituted by fluorine, chlorine, $C_1$-$C_4$-alkyl, $C_1$-$C_4$-alkoxy, trifluoromethyl or trifluoromethoxy, and Y—denotes pyridyl, or represents a group of the formula —$NR^9R^{10}$, in which $R^9$ and $R^{10}$ are identical or different and represent hydrogen or straight-chain or branched alkyl or alkenyl in each case having up to 8 carbon atoms which may be substituted by fluorine, chlorine, hydroxyl, $C_1$-$C_4$-alkoxy, $C_1$-$C_4$-alkylthio, $C_1$-$C_4$-alkylcarbonyl, carboxyl or $C_1$-$C_6$-alkoxycarbonyl, or by phenyl which may in turn be substituted by trifluoromethyl, $C_1$-$C_2$-alkyl, fluorine, chlorine or $C_1$-$C_2$-alkoxy, or represent cycloalkyl having 3 to 8 carbon atoms, or represent phenyl which may be monosubstituted or disubstituted by identical or different substituents from the series comprising nitro, cyano, fluorine, chlorine, bromine, $C_1$-$C_4$-alkyl, $C_1$-$C_4$-alkoxy, $C_1$-$C_4$-alkylthio, trifluoromethyl, trifluoromethoxy, difluoromethoxy, trifluoromethylthio, amino or alkylamino having up to 4 carbon atoms, or $R^9$ and $R^{10}$ together form a 5- to 7-membered saturated or unsaturated heterocyclic ring which may additionally contain an oxygen or sulphur atom or an additional nitrogen atom which is optionally substituted by an $R^{11}$ radical, in which $R^{11}$—represents hydrogen or represents a straight-chain or branched, saturated or unsaturated alkyl group having up to 4 carbon atoms, which is optionally substituted by phenyl which may in turn be substituted by fluorine, chlorine, $C_1$-$C_2$-alkyl, $C_1$-$C_2$-alkoxy or $C_1$-$C_2$-haloalkyl, or represents phenyl which is optionally substituted by fluorine, chlorine, cyano, $C_1$-$C_2$-alkyl, $C_1$-$C_2$-alkoxy or $C_1$-$C_2$-haloalkyl, and their physiologically acceptable salts.

The compounds of the general formula (Ia) are particularly preferred in which $R^1$ and $R^2$ are identical or different and represent hydrogen, cyclopropyl, cyclopentyl or cyclohexyl, or represent straight-chain or branched alkyl or alkenyl having up to 8 carbon atoms, which is optionally substituted by fluorine, chlorine, hydroxyl, $C_1$-$C_4$-alkoxy, $C_1$-$C_4$-alkylthio, carboxyl, $C_1$-$C_4$-alkoxycarbonyl or by phenyl which may in turn be substituted by chlorine, fluorine, methyl or methoxy, or represent phenyl which may be substituted by fluorine, chlorine, methyl, ethyl, methoxy, trifluoromethyl or trifluoromethoxy, $R^3$ and $R^4$—represent methyl and X—represents a straight-chain, branched or cyclic, saturated or unsaturated hydrocarbon radical having up to 8 carbon atoms, which is optionally interrupted by an oxygen, sulphur or nitrogen atom, or by an —N—$R^8$ radical, in which $R^8$—denotes hydrogen, or represents methyl, ethyl, benzyl, phenethyl or phenyl which is optionally substituted by fluorine, chlorine, methyl, methoxy, trifluoromethyl or trifluoromethoxy, Y—represents pyridyl, or represents a group of the formula —$NR^9R^{10}$ in which $R^9$ and $R^{10}$ are identical or different and represent hydrogen or straight-chain or branched alkyl or alkenyl having up to 4 carbon atoms which may be substituted by fluorine, chlorine, hydroxyl, $C_1$-$C_4$-alkoxycarbonyl or by phenyl which may in turn be substituted by fluorine, chlorine, trifluoromethyl, methyl or methoxy, or represent cyclopropyl, cyclopentyl or cyclohexyl, or represent phenyl which may be monosubstituted or disubstituted by identical or different substituents from the series comprising fluorine, chlorine, methyl, ethyl, methoxy, ethoxy, methylthio, trifluoromethyl, trifluoromethoxy, difluoromethoxy, amino, $C_1$-$C_2$-alkylamino or $C_1$-$C_2$-dialkylamino, or $R^9$ and $R^{10}$ together form a 5- to 7-membered saturated ring which may additionally contain an oxygen, sulphur or an additional nitrogen atom which is optionally substituted by an $R^{11}$ radical in which $R^{11}$—represents hydrogen, $C_1$-$C_4$-alkyl, benzyl or phenethyl, or represents phenyl which may be substituted by fluorine, chlorine, methyl or methoxy, and their physiologically acceptable salts.

Very particularly preferred are compounds of the general formula (Ia) and (I) in which $R^1$ and $R^2$ are identical or different and each represent hydrogen, alkyl with 1 to 4 carbon atoms, cyclopropyl or cyclopentyl, $R^3$ $R^4$ represent methyl, X represents straight-chain or branched alkyl with up to 4 carbon atoms, and Y represents pyridyl or morpholino or represents a group of the formula $NR^9R^{10}$ in which $R^9$ and $R^{10}$ are identical or different and represent hydrogen, alkyl with up to 4 carbon atoms or benzyl, and their physiologically acceptable salts.

The new compounds of the formula (Ia) according to the invention also show an unforeseeable useful spectrum of pharmacological action. They influence the contractility of the heart, the tone of the smooth musculature and the electrolyte and fluid balance.

They can therefore be employed in medicaments for the treatment of pathologically changed blood pressure and cardiac insufficiency, and also as coronary therapeutics.

Moreover, they can be employed for the treatment of cardiac arrhythmias, renal insufficiency, cirrhosis of the liver, ascites, pulmonary oedema, cerebral oedema, oedema of pregnancy, glaucoma or diabetes mellitus.

The compounds of the general formula (I) or (Ia) according to the invention

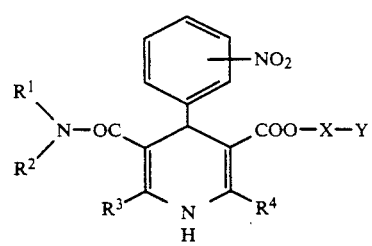

in which $R^1$, $R^2$, $R^3$, $R^4$, X and Y have the abovementioned meanings, are obtained by a process in which

[A] aldehydes of the general formula (II)

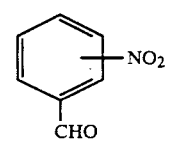

and β-ketocarboxylic acid esters of the general formula (III)

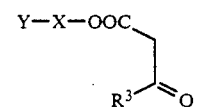

in which $R^3$, X and Y have the abovementioned meanings, if desired after isolating the ylidene compound resulting therefrom of the general formula (IV)

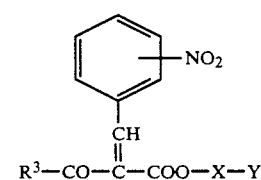

in which $R^3$, X and Y have the abovementioned meaning are reacted with β-ketocarboxylic acid amides of the general formula (V)

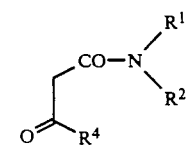

in which $R^1$, $R^2$ and $R^4$ have the abovementioned meanings, and ammonia or directly with the β-aminocrotonic acid amides prepared therefrom of the general formula (VI)

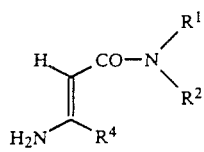

(VI)

in which
$R^1$, $R^2$ and $R^4$ have the abovementioned meanings, or by a process in which

[B] aldehydes of the general formula (II) and β-ketocarboxylic acid amides of the general formula (V) or ylidene compounds thereof of the general formula (VII)

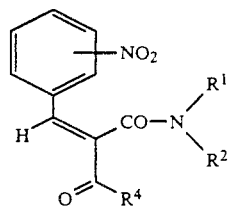

(VII)

in which
$R^1$, $R^2$ and $R^4$ have the abovementioned meanings, are reacted with β-ketocarboxylic acid esters of the general formula (III) and ammonia or directly with the aminocrotonic acid esters prepared therefrom of the general formula (VIII)

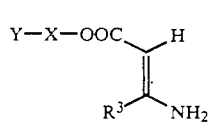

(VIII)

in which
$R^3$, X and Y have the abovementioned meanings, or compounds of the general formula (I) in which $R^1$, $R^2$, $R^3$, $R^4$ and X have the abovementioned meanings, and
Y represents a group of the formula $NR^9R^{10}$ and $R^9$ and/or $R^{10}$ denote reactive hydrogen, are expediently obtained by a process in which

[C] benzylidene compounds of the general formula (VII) are first reacted with compounds of the general formula

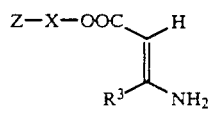

(VIIIa)

in which
$R^3$ and X have the abovementioned meanings,
Z—represents an acylated amino protective group, preferably tert.-butoxycarbonylamino or phthalimide,
to give compounds of the general formula (IX)

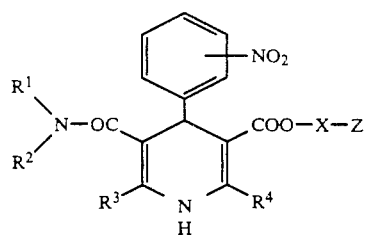

(IX)

in which
$R^1$, $R^2$, $R^3$, $R^4$ and X have the abovementioned meanings, and
Z—represents the group

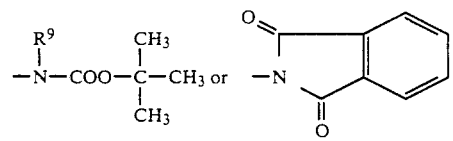

deblocked by known methods in a further step and the intermediate compounds of the formula (IXa) obtained

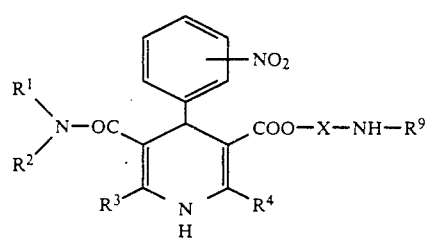

(IXa)

in which $R^1$, $R^2$, $R^3$, $R^4$, X and $R^9$ have the abovementioned meaning
are further reacted to give compounds of the general formula (I) in which
Y—represents the group $NR^9R^{10}$, in which $R^9$ and $R^{10}$ have the abovementioned meanings, with the proviso that $R^9$ and/or $R^{10}$ are not hydrogen,
or by a process in which

[D] dihydropyridinemonocarboxylic acids of the general formula (Xa) or (Xb)

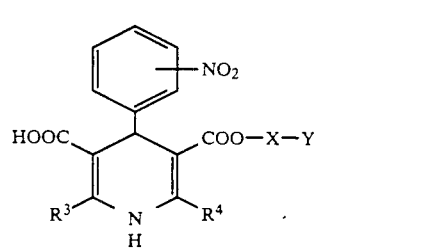

(Xa)

-continued

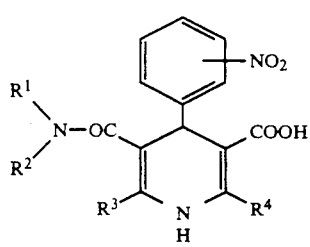

in which
R$^1$, R$^2$, R$^3$, R$^4$, X and Y have the abovementioned meanings, are reacted, if desired via reactive acid derivatives, with amines of the general formula (XIa)

 (XIa)

in which
R$^1$ and R$^2$ have the abovementioned meanings, or with compounds of the formula (XIb)

HO—X—Y          (XIb)

in which
X and Y have the abovementioned meanings, where in each case only (Xa) is reacted with (XIa) and (Xb) with (XIb).

Examples of reactive acid derivatives which may be mentioned are:

activated esters, hydroxysuccinimide esters, acid imidazolides, acid halides, mixed anhydrides or reaction in the presence of cyclohexylcarbodiimide.

Depending on the type of starting material used, the synthesis variants for the compounds according to the invention can be represented by the following equations:

Variant A:

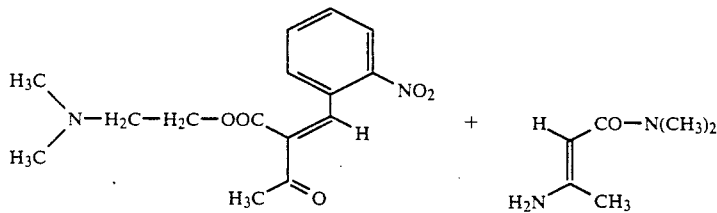

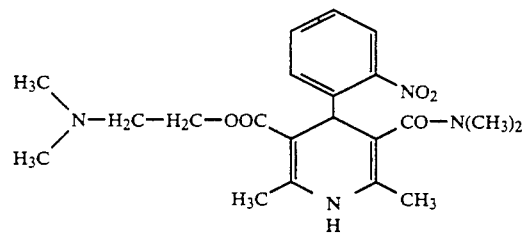

Variant B:

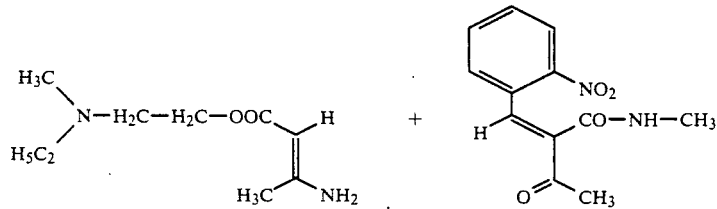

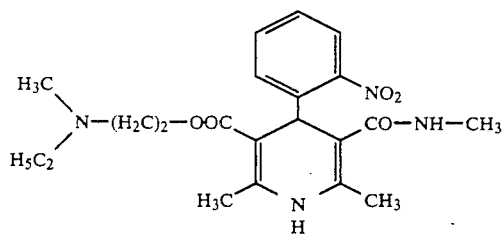
Variant D:
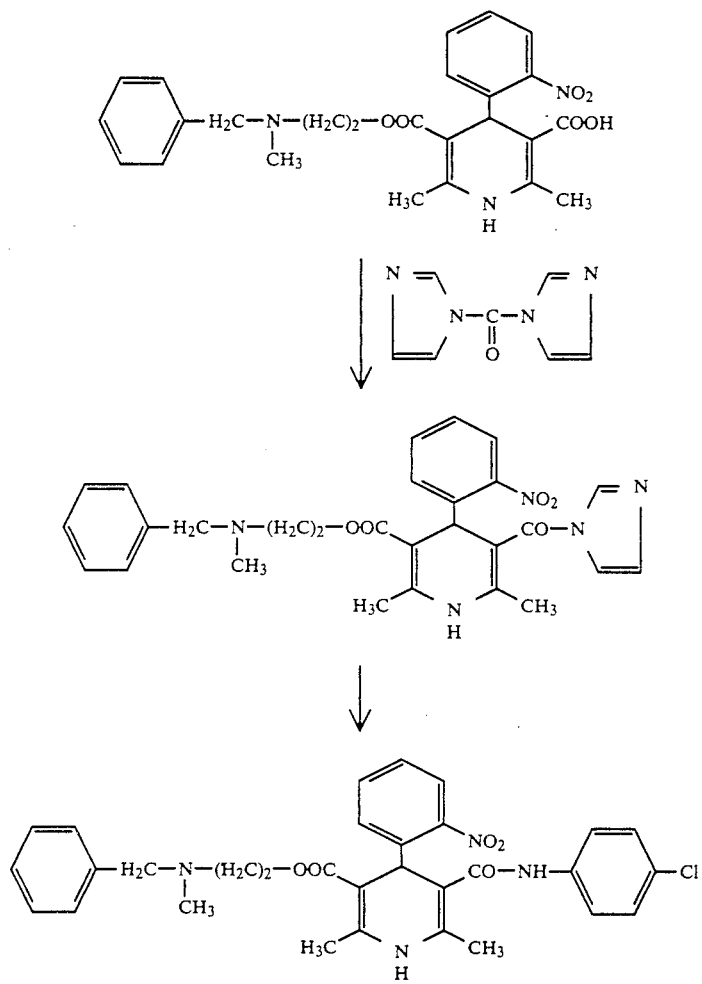
[D]
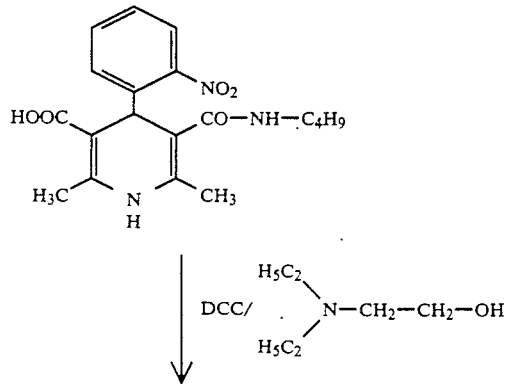

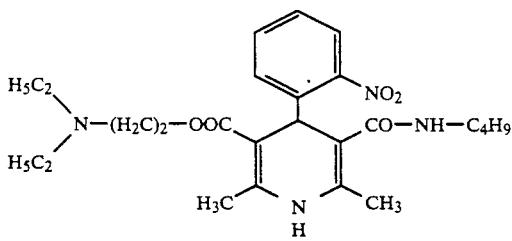

Process Variants A-D

Possible solvents are water or all inert organic solvents which do not change under the reaction conditions. These preferably include alcohols such as methanol, ethanol, propanol, isopropanol, ethers such as diethyl ether, dioxane, tetrahydrofuran, glycol monomethyl ether or glycol dimethyl ether, or amides such as dimethylformamide, dimethylacetamide or hexamethylphosphoramide, or glacial acetic acid, dimethyl sulphoxide, acetonitrile or pyridine.

The reaction temperatures can be varied within a relatively wide range. In general, the reaction is carried out between +10° C. and +150° C., preferably between +20° C. and +100° C., in particular at the boiling point of the respective solvent.

The reaction can be carried out at atmospheric pressure, and also at elevated or reduced pressure. In general, it is carried out at atmospheric pressure.

When carrying out process variants A-D according to the invention, the ratio of the substances participating in the reaction is arbitrary. In general, however, the reaction is carried out using molar amounts of reactants. The substances according to the invention are preferably isolated and purified in such a way that the solvent is distilled off in vacuo and the residue, if desired first obtained crystalline after ice cooling, is recrystallized from a suitable solvent. In some cases, it may be necessary to purify the compounds according to the invention by chromatography.

The aldehydes of the general formula (II) employed as starting substances are known or can be prepared by known methods [DOS 2,165,260; 2,401,665; T. D. Harris, G. P. Roth, J. Org. Chem. 44, 2004 (1979); W. J. Dale, H. E. Hennis, J. Am. Chem. Soc. 78, 2543 (1956); Chem. Abstr. 59, 13929 (1963)].

The β-ketocarboxylic acid esters of the general formula (III) employed as starting substances are known or can be prepared by known methods [D. Borrmann in Houben Weyl's "Methoden der organischen Chemie" ("Methods of organic chemistry") Vol. VII/4, 230 (1968); Y. Oikawa, K. Sugano, O. Yonemitsu, J. Org. Chem. 43, 2087 (1978)].

The enamines of the general formulae (VI) and (VIII) employed as starting substances are known or can be prepared by known methods [DOS 2,228,377; F. A. Glickman, A. C. Cope, J. Am. Chem. Soc. 67, 1017 (1945)].

Process variant D according to the invention is carried out following the method known from the literature for the conversion of carboxylic acids into carboxylic acid amides. In this method, the carboxylic acid is first converted into an activated form such as, for example, the acid chloride or the imidazolide, which is either isolated as such and reacted in a second reaction step or is amidated directly in situ to give the compounds according to the invention. Examples of activating reagents which may be mentioned in addition to the inorganic halides such as thionyl chloride, phosphorus trichloride or phosphorus pentachloride, or carbonyl diimidazole, are carbodiimides such as cyclohexylcarbodiimide or 1-cyclohexyl-3-[2-(N-methyl-morpholino)ethyl]carbodiimide p-toluenesulphonate or N-hydroxyphthalimide or N-hydroxy-benzotriazole in the presence of dicyclohexylcarbodiimide. Naturally, the dihydropyridine monocarboxylic acids may also be employed in the form of their salts. [The method of amidation is described, for example, in: Fieser & Fieser, Reagents for Organic Synthesis, John Wiley & Sons Inc. (1967), pages 231-236; J. C. Shihan and G. P. Hess, J. Am. Chem. Soc. 77, 1067 (1955), U. Goodman, G. W. Kenner, Adv. in Protein Chem. 12, 488 (1957); W. A. Bonner, P. I. McNamee, J. Org. Chem. 26, 254 (1961); H. A. Staab, Angew. Chemie Int. Ed. 1, 351 (1962); Fieser & Fieser, Reagents for Organic Synthesis, John Wiley & Sons Inc. 1967, 116, 114; H. C. Beyerman, U. O. van der Brink, Re. Trav. 80, 1372 (1961); C. A. Buehler, D. E. Pearson, John Wiley & Sons, Volume I (1970), pages 895 ff, Volume II, (1977)].

Possible solvents for process variants D are, in addition to water, all inert organic solvents which do not change under the reaction conditions. These preferably include ethers such as diethyl ether, dioxane, tetrahydrofuran, glycol monomethyl ether or glycol dimethyl ether, or halogenated hydrocarbons such as dichloromethane, trichloromethane or tetrachloromethane, or amides such as dimethylformamide, dimethylacetamide or hexamethylphosphoramide, or hydrocarbons such as benzene, toluene or xylene, or acetonitrile, nitromethane, pyridine, dimethyl sulphoxide or ethyl acetate. Mixtures of the solvents mentioned may also be used. If the activated intermediates of the dihydropyridine monocarboxylic acids are isolated, the amines of the formula (XIa) may also be used alone as diluents.

The reaction temperatures can be varied within a wide range. In general the reaction is carried out in a range from −70° C. to +140° C., preferably from −20° C. to +100° C.

The reaction can be carried out at atmospheric pressure, and also at elevated or reduced pressure. In general, the reaction is carried out at atmospheric pressure.

When carring out process variant D according to the invention, the ratio of the substances participating in the reaction is arbitrary. In general, however, the reaction is carried out using molar amounts of the reactants. However, it has proved favorable to employ the amine in a 5- to 10-fold molar excess. The amine is particularly expediently employed directly in a large excess as the solvent.

The amino protective group is removed in a manner known per se, for example under acidic conditions, or if Z represents the phthalimide radical, the protective group is customarily removed using hydrazine hydrate in organic solvents such as ethers, for example tetrahydrofuran or dioxane, or alcohols, for example methanol, ethanol or isopropanol.

The amines of the general formulae (XIa) and (XIb) employed as starting substances are known or can be prepared by known methods [Houben Weyl's "Methoden der organischen Chemie" ("Methods of organic chemistry") Vol. XI/1; Paulsen, Angewandte Chemie 78, 501–566 (1966)].

The invention also relates to the new intermediates of the general formulae (IX) and (IXa)

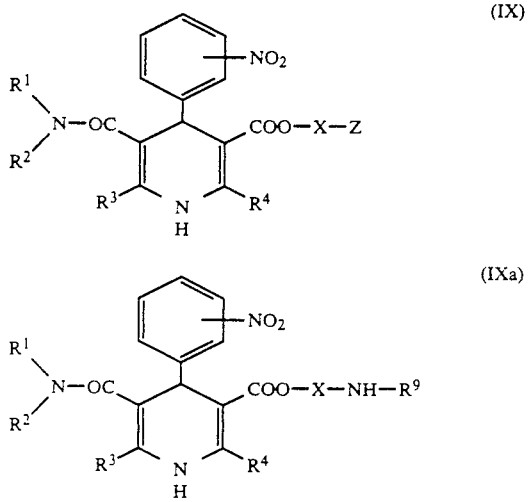

in which $R^1$, $R^2$, $R^3$, $R^4$, X, Z and $R^9$ have the abovementioned meanings.

These new intermediates of the general formulae (IX) and (IXa) are prepared by cyclizing benzylidene compounds of the general formula (VII) with compounds of the general formula (VIIIa), if desired in the presence of inert organic solvents, and deblocking the compound of the formula (IX) obtained by known methods to give compounds (IXa) if desired by removing the protective group (Z).

The new and known compounds of the formula (I) and (Ia) show an unforeseeable, useful pharmacological spectrum of action. They influence the contractility of the heart, the tone of the smooth musculature and the electrolyte and fluid balance.

They can therefore be employed in medicaments for the treatment of pathologically changed blood pressure and cardiac insufficiency, and also as coronary therapeutics.

Moreover, they can be employed for the treatment of cardiac arrhythmias, renal insufficiency, cirrhosis of the liver, ascites, pulmonary oedema, cerebral oedema, oedema of pregnancy, glaucoma or diabetes mellitus.

The cardiac action of the compounds according to the invention was discovered on the isolated, stimulated capillary muscle of the guinea pig heart. For this purpose, the experimental animals (200 g guinea pigs of both sexes) were sacrificed, the thorax was opened and the heart was removed. For the experiments, the smallest possible capillary muscles were then in each case disected out of the right ventricle and fixed horizontally in an organ bath. In this bath, one end of the muscle was held by two metal electrodes which were simultaneously used for stimulating the preparation, while the other end of the muscle was connected via a thread to a force transducer. The capillary muscle was stimulated supraliminally using a frequency of 1 Hz. A Krebs-Henseleit solution (concentration in mM: NaCl 118; NaHCO$_3$ 25; KCl 10; KH$_2$PO$_4$ 1.2; MgSO$_4$ 1.2; CaCl$_2$ 1.8; glucose 10, pH 7.4) continuously flowed through the organ bath having a volume of about 2 ml at a rate of 4 ml/min at a temperature of 32° C. The contractions of the capillary muscle were measured isometrically by means of the attached force transducer and recorded on a recording instrument.

The substances according to the invention were dissolved in the Krebs-Henseleit solution in a concentration of 10 μg/ml, if necessary using a solubilizer (DMSO up to a concentration of 0.5%). The dihydropyridine carboxamides according to the invention showed an inhibition of the contractility of the capillary muscle of more than 10% relative to the control values.

In order to test the renal effect, the substances were administered orally to conscious male Wistar rats. After loading with physiological saline solution, sodium excretion was measured in metabolic cages.

The new active compounds may be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient to achieve the dosage range indicated.

The formulations are prepared, for example, by extending the active compound with solvents and/or excipients, optionally using emulsifiers and/or dispersants, where, for example, in the case of the use of water as a diluent, if appropriate organic solvents may be used as auxiliary solvents.

Examples of auxiliaries which may be mentioned are: water, non-toxic organic solvents, such as paraffins, (for example mineral oil fractions), vegetable oils (for example groundnut/sesame oil), alcohols, (for example: ethyl alcohol, glycerol), excipients, such as, for example, ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates, arylsulphonates), detergents (for example lignin-sulphite waste liquors, methyl cellulose, starch and polyvinylpyrrolidone) and lubricants (for example magnesium stearate, talc, stearic acid and sodium lauryl sulphate).

Administration is carried out in a customary manner, preferably orally or parenterally, in particular perlingually or intravenously. In the case of oral administration, tablets may, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc may additionally be used for tableting. In the case of aqueous suspensions, various flavo enhancers or colorants may be added to the active compounds in addition to the abovementioned auxiliaries.

In the case of parenteral administration, solutions of the active compounds may be employed using suitable liquid carrier materials.

In general, it has proved advantageous on intravenous administration to administer amounts of about 0.001 to 1 mg/kg, preferably about 0.01 to 0.5 mg/kg of body weight to obtain effective results, and on oral administration the dosage is about 0.01 to 20 mg/kg, preferably 0.1 to 10 mg/kg of body weight.

In spite of this, it may sometimes be necessary to deviate from the amounts mentioned, depending on the body weight or the type of application route, on individual behavior towards the medicament, the manner of its formulation and the point in time or interval at which administration takes place. Thus, in some cases it may be sufficient to manage with less than the minimum amount previously mentioned, whereas in other cases the upper limit mentioned must be exceeded. In the case of administration of larger amounts, it may be advisable to divide these into a number of individual doses over the day.

PREPARATION EXAMPLES

Process Variant D

Example 1

N-Ethyl 3-(2-N-benzyl-N-methyl-ethoxycarbonyl)-1,4-dihydro-2,6-dimethyl-4-(3-nitrophenyl)-pyridine-5-carboxamide hydrochloride

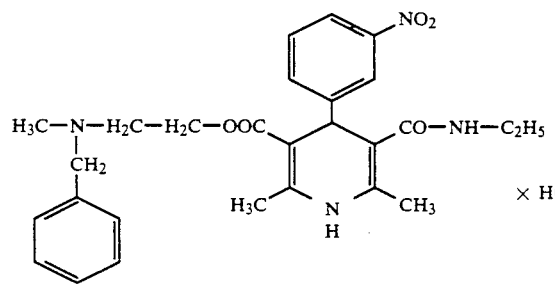

4 g (7.5 mmol) of 3-(2-N-benzyl-N-methyl-ethoxycarbonyl)-1,4-dihydro-2,6-dimethyl-4-(3-nitrophenyl)-5-carboxylic acid imidazolide are stirred overnight with 40 ml of 50% strength ethylamine solution. The mixture is concentrated, the residue is taken up in ethyl acetate and the solution is washed twice with water, dried and concentrated. The evaporation residue obtained is purified by means of a silica gel column. The clean fractions are concentrated and converted into the hydrochloride. 1.1 g of colorless crystals of melting point 150° C. with decomposition are obtained.

Example 2

Process Variant A

N-Cyclopentyl 1,4-dihydro-2,6-dimethyl-3-($\beta$ -N-morpholinoethoxycarbonyl)-4-(2-nitrophenyl)-pyridine-5-carboxamide

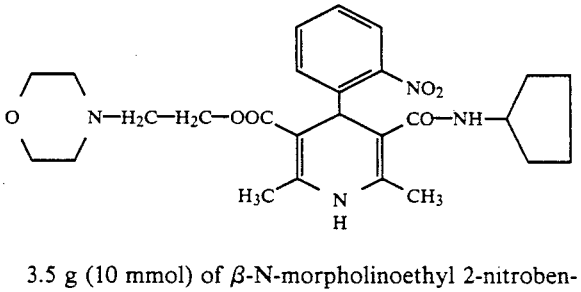

3.5 g (10 mmol) of $\beta$-N-morpholinoethyl 2-nitrobenzylidene-acetoacetate are boiled for 4 hours under argon with 1.68 g (10 mmol) of N-cyclopentyl $\beta$-aminocrotonamide in 25 ml of isopropanol. The mixture is cooled, and the crystals which have precipitated are filtered off with suction and washed with isopropanol. 3.25 g of orange-colored crystals of melting point 193° C. are obtained.

The examples listed in the following table were prepared analogously to the directions for the Process Variants A and D:

TABLE 1

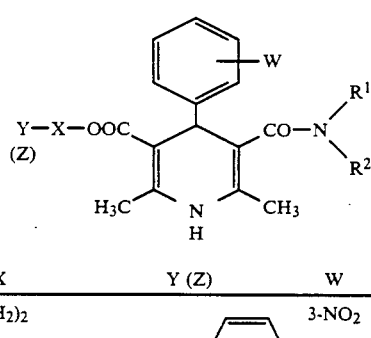

| Ex. | $R^1$ | $R^2$ | X | Y (Z) | W | Salt | M.p. | $R_f$ |
|---|---|---|---|---|---|---|---|---|
| 3 | $CH_3$ | H | $(CH_2)_2$ | —N(CH₃)—CH₂—C₆H₅ | 3-NO₂ | — | Foam | 0.38 (a) 0.56 (b) |
| 4 | cyclopropyl | H | $(CH_2)_2$ | —N(CH₃)—CH₂—C₆H₅ | 3-NO₂ | HCl | 155° C. | 0.42 (a) 0.58 (b) |
| 5 | $CH_3$ | H | $(CH_2)_2$ | —N(CH₃)—CH₂—C₆H₅ | 2-NO₂ | — | 152–154° C. | 0.43 (a) 0.58 (b) |

TABLE 1-continued

Structure: 4-phenyl-1,4-dihydropyridine with W substituent on phenyl, 3-position CO-NR¹R², 5-position COO-X-Y(Z), 2,6-dimethyl, NH.

| Ex. | R¹ | R² | X | Y (Z) | W | Salt | M.p. | R_f |
|---|---|---|---|---|---|---|---|---|
| 6 | cyclopentyl | H | (CH₂)₂ | —N(CH₃)—CH₂—C₆H₅ | 2-NO₂ | — | 164–165° C. | 0.55 (a) 0.60 (b) |
| 7 | cyclopropyl | H | (CH₂)₂ | —N(CH₃)—CH₂—C₆H₅ | 2-NO₂ | — | 140–149° C. | 0.46 (a) 0.60 (b) |
| 8 | C₃H₇ | H | (CH₂)₂ | —N(CH₃)—CH₂—C₆H₅ | 2-NO₂ | — | 163–165° C. | 0.53 (a) 0.01 (b) |
| 9 | CH₃ | H | (CH₂)₂ | morpholino | 2-NO₂ | — | 154–157° C. | 0.22 (a) 0.48 (b) |
| 10 | CH₃ | H | (CH₂)₂ | —N(CH₃)—CH₂—CH₃ | 2-NO₂ | — | 128–130° C. | 0.1 (a) 0.16 (b) |
| 11 | C₃H₇ | H | (CH₂)₂ | morpholino | 2-NO₂ | — | 139–141° C. | 0.35 (a) 0.56 (b) |
| 12 | cyclopropyl | H | (CH₂)₂ | morpholino | 2-NO₂ | — | 129–131° C. | 0.27 (a) 0.54 (b) |
| 13 | cyclopropyl | H | (CH₂)₂ | —N(CH₃)—CH₂—CH₃ | 2-NO₂ | — | | 0.1 (a) |
| 14 | cyclopropyl | H | (CH₂)₂ | 3-pyridyl | 2-NO₂ | — | 196–198° C. | 0.20 (a) 0.55 (b) |
| 15 | CH₃ | H | (CH₂)₂ | 3-pyridyl | 2-NO₂ | — | 192–194° C. | 0.14 (a) 0.52 (b) |
| 16 | C₂H₅ | H | (CH₂)₂ | morpholino | 2-NO₂ | — | 147° C. | 0.27 (a) 0.53 (b) |
| 17 | C₂H₅ | H | (CH₂)₂ | —N(CH₃)—CH₂—C₆H₅ | 2-NO₂ | — | 147–149° C. | |

TABLE 1-continued

| Ex. | R¹ | R² | X | Y (Z) | W | Salt | M.p. | $R_f$ |
|---|---|---|---|---|---|---|---|---|
| 18 | $C_2H_5$ | H | $(CH_2)_2$ | 3-pyridyl | 2-$NO_2$ | — | 160° C. | |
| 19 | $C_2H_5$ | H | $(CH_2)_2$ | phthalimido | 3-$NO_2$ | — | 108–110° C. | 0.67 (c) |
| 20 | cyclopropyl | H | $(CH_2)_2$ | phthalimido | 3-$NO_2$ | — | 123–125° C. | 0.64 (c) |
| 21 | $C_2H_5$ | H | $(CH_2)_2$ | phthalimido | 2-$NO_2$ | — | 120–122° C. | 0.57 (c) |
| 22 | $C_2H_5$ | H | $CH_3$-CH-$CH_2$- | phthalimido | 3-$NO_2$ | — | | 0.64 (c) |
| 23 | cyclopropyl | H | $CH_3$-CH-$CH_2$- | phthalimido | 3-$NO_2$ | — | 127–131° C. | 0.60 (c) |
| 24 | $C_2H_5$ | H | $CH_3$-CH-$CH_2$- | phthalimido | 2-$NO_2$ | — | | |

Example 25

N-Cyclopropyl 3-(2-aminomethoxycarbonyl)-1,4-dihydro-2,6-dimethyl-4-(3-nitrophenyl)-pyridine-5-carboxamide

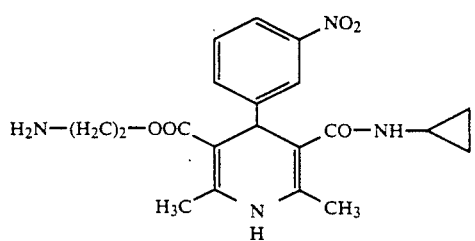

A solution of 9.7 g (18.7 mmol) of N-cyclopropyl 1,4-dihydro-2,6-dimethyl-4-(3-nitrophenyl)-3-(2-phthalimidoethoxycarbonyl)-pyridine-5-carboxamide (Example 20) and 93.5 mmol of hydrazine hydrate in 200 ml of ethanol was heated under reflux for 1 h. The mixture was cooled and the precipitate was filtered off. The residue was then washed with methylene chloride and the organic phase was concentrated in vacuo. After addition of methylene chloride, the mixture was washed once with a 2 N solution of potassium hydroxide and 3 times with water. The organic phase was dried using sodium sulphate and concentrated in vacuo. The product crystallized on triturating with ether.

Yield: 5.95 g (82% of theory)
Melting point: 55-57° C.
$R_f$: 0.17$^{d)}$

The compounds listed in Table 2 were prepared analogously to the directions of Example 25:

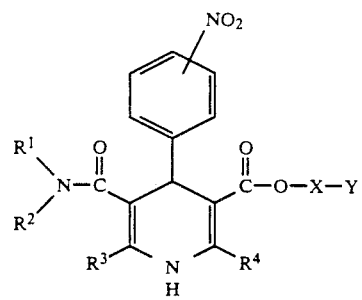

in which
$R^1$ and $R^2$ are identical or different and each represent hydrogen, alkyl with 1 to 4 carbon atoms, cyclopropyl or cyclopentyl,
$R^3$ and $R^4$ represent methyl,

TABLE 2

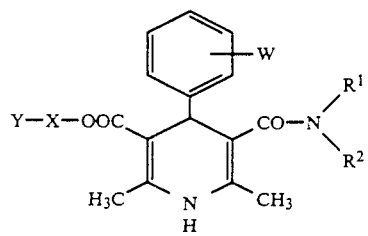

| Ex. | $R^1$ | $R^2$ | X | Y | W | Salt | M.p. | $R_f$ |
|---|---|---|---|---|---|---|---|---|
| 26 | $C_2H_5$ | H | —(CH$_2$)$_2$— | —NH$_2$ | 3-NO$_2$ | — | 144–146° C. | 0.18 (d) |
| 27 | $C_2H_5$ | H | —CH(CH$_3$)—CH$_2$— | —NH$_2$ | 3-NO$_2$ | — | 169–173° C. Both diastereomeric forms | 0.52 (d) |
| 28 | cyclopropyl | H | —CH(CH$_3$)—CH$_2$— | —NH$_2$ | 3-NO$_2$ | — | 185–186° C. Both diastereomeric forms | |

The following solvents were listed under (a)–(d):
(a) toluene/acetone (1:1)
(b) toluene/ethanol (3:1)
(c) methylene chloride/methanol (10:1)
(d) methylene chloride/methanol (5:1)

It will be understood that the specification and examples are illustrative but not limitative of the present invention and that other embodiments within the spirit and scope of the invention will suggest themselves to those skilled in the art.

What is claimed is:

1. A method of controlling cardiac arrhythmias in a patient in need thereof which comprises administering to such patient an amount effective therefor of a 4-nitrophenyldihydropyridine amide of the formula X represents straight-chain or branched alkyl with up to 4 carbon atoms, and
Y represents pyridyl or morpholino or represents a group of the formula $NR^9R^{10}$ in which
$R^9$ and $R^{10}$ are identical or different and represent hydrogen, alky with up to 4 carbon atoms or benzyl.

2. The method according to claim 1, wherein such compound is N-cyclopropyl 3-(2-N-benzyl-N-methyl-ethoxycarbonyl)-1,4-dihydro-2,6-dimethyl-4-(2-nitrophenyl)-pyridine-5-carboxamide of the formula

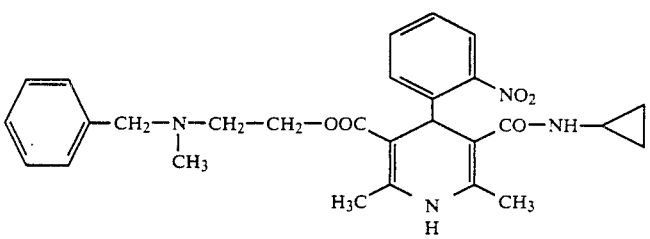

or a physiologically tolerated salt thereof.

3. The method according to claim 1, wherein such compound is N-propyl 3-(2-N-benzyl-N-methyl-ethoxycarbonyl)-1,4-dihydro-2,6-dimethyl-4-(2-nietrophenyl)-pyridine-5-carboxamide of the formula

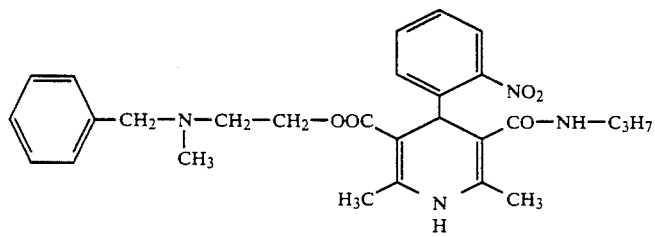

or a physiologically tolerated salt thereof.

4. The method according to claim 1, wherein such compound is N-ethyl-3-(2N-benzyl-N-methyl-ethoxycarbonyl)-1,4-dihydro-2,6-dimethyl-4-(2-nitrophenyl)-pyridine-5-carboxamide of the formula

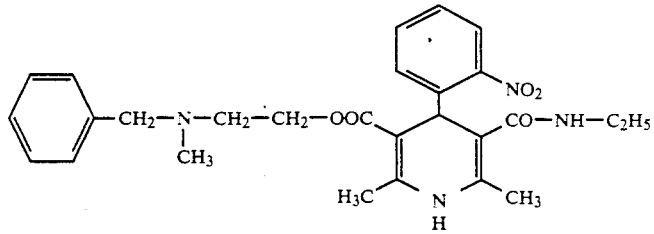

or a physiologically tolerated salt thereof.

* * * * *